United States Patent [19]

Loev et al.

[11] Patent Number: 4,505,920

[45] Date of Patent: Mar. 19, 1985

[54] CERTAIN N-SUBSTITUTED-4-ARYL-3,5-PYRIDINE DICARBOXYLATES AND THEIR ANTIHYPERTENSIVE USE

[75] Inventors: Bernard Loev, Scarsdale; Howard Jones, Ossining, both of N.Y.; John T. Suh, Greenwich, Conn.

[73] Assignee: USV Pharmaceutical Corporation, Tarrytown, N.Y.

[21] Appl. No.: 471,916

[22] Filed: Mar. 3, 1983

[51] Int. Cl.³ .................. C07D 403/06; A61K 31/455
[52] U.S. Cl. .................................... 514/341; 546/279; 546/281; 546/321; 514/343
[58] Field of Search ................. 546/281, 279; 424/266

[56] References Cited

U.S. PATENT DOCUMENTS 4,419,518 12/1983 Kamibayashi et al. ............. 546/279

OTHER PUBLICATIONS

Iwanami et al., Chemical Abstracts, vol. 86, No. 7, Abst. 43570d, Feb. 14, 1977.

Burger, Medicinal Chemistry, Third Edition, Part I, p. 593, Wiley–Interscience (1971).

*Primary Examiner*—Alan L. Rotman

[57] ABSTRACT

Unsaturated heterocyclic dihydropyridine of the formula

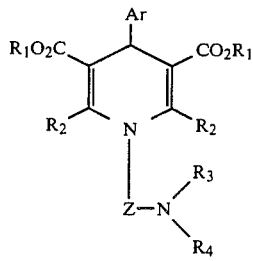

wherein $R_3$ and $R_4$ together with the N to which they are attached form an unsaturated heterocyclic group, have been found to possess useful anti-hypertensive activity.

10 Claims, No Drawings

CERTAIN N-SUBSTITUTED-4-ARYL-3,5-PYRIDINE DICARBOXYLATES AND THEIR ANTIHYPERTENSIVE USE

This invention relates to new anti-hypertensive agents and more particularly to certain new substituted 1,4-dihydropyridines possessing useful anti-hypertensive activity.

Substituted 1,4-dihydropyridines are known and have been described in the literature as vasodilating agents. 1,4-Dihydropyridines having vasodilating activity are characterized by the presence of alkyl substituents in the 2 and 6 positions of the pyridine ring and carbalkoxy groups in the 3,5-positions usually with a substituent, most commonly phenyl or substituted phenyl, in the 4-position. To increase the water-solubility of these compounds, M. Iwanami, et al. [Chem. Pharm. Bull. 27 (6), 1526-1440 (1979)] described the effect of N-substitution of the pyridine ring nitrogen with, inter alia, aminoalkylene groups such as pyrrolidinoethyl and dimethylaminoethyl. Thus, water-solubility determinations with compounds such as diethyl 1,4-dihydro-4-(3-nitrophenyl)-2,6-dimethyl-1-(2-pyrrolidinoethyl)-3,5-pyridinedicarboxylate and the corresponding1 1-(2-dimethylaminoethyl) compound were determined as was the potency thereof as vasodilators but these compounds were determined to be of lower potency than known compounds such as the corresponding 1-ethoxymethyl compound.

Japanese specification No. 70767/76 describes as antihypertensive and vasodilating agents 1,4-dihydropyridines of the formula

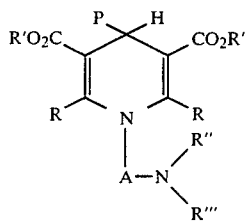

in which R is alkyl; P is substituted (mono or di-) phenyl, pyridyl, furyl, or thienyl in which the substituents are H, halogen, —CN, —NO$_2$, —NH$_2$, —N(CH$_3$)$_2$, carboxyl, methoxy, ethoxy, butoxy, sulfonyl, methylsulfonyl or acetyl; R' is alkyl, aralkyl, methyl, ethyl, isopropyl, t-butyl, ethoxyethyl, benzyl, phenethyl, or 4-methoxybenzyl; A is alkylene; and R" and R''' are each alkyl and, when taken together, form a pyrrolidine ring with the N to which they are attached.

U.S. Pat. No. 4,258,042 describes N-morpholinodihydropyridines of the formula

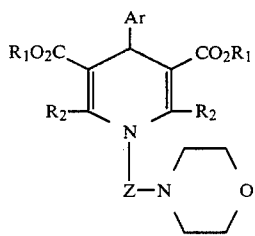

wherein Ar is heteroaryl, cycloalkyl or

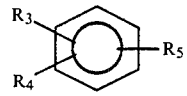

wherein each of R$_3$, R$_4$ and R$_5$ is H, alkyl, aryl, halo, lower alkoxy, nitro, amino, alkylmercapto, cyano, carboxy, carbalkoxy, sulfamyl, trifluoromethyl, hydroxy, acyloxy, methanesulfonyl, alkylamino or acylamino; and R$_3$ and R$_4$, when taken together, form a methylenedioxy; Z is alkylene containing 1 to about 5 carbon atoms in the principal chain; and each R$_1$ and R$_2$ is alkyl; and acid addition salts thereof.

The new compounds of the present invention are unsaturated heterocyclic dihydropyridines of the formula:

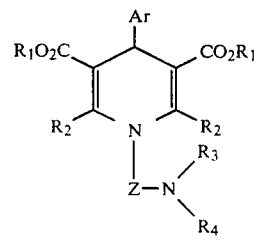

FORMULA I wherein Ar is heteroaryl, cycloalkyl having from 3 to 7 carbon atoms, naphthyl, indanyl, indenyl, tetrahydronaphthyl, or a radical of the formula

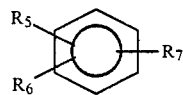

wherein each of R$_5$, R$_6$ and R$_7$ is independently H, alkyl, aryl, halo, lower alkoxy, nitro, amino, alkylmercapto, cyano, carboxy, carbalkoxy, sulfamyl, trifluoromethyl, hydroxy, acyloxy, methanesulfonyl, alkylamino or acylamino; and R$_5$ and R$_6$ when taken together, form a methylenedioxy; Z is alkylene containing 1 to about 5 carbon atoms in the principal chain; each R$_1$ is independently hydrogen, alkyl or alkoxyalkyl, with the proviso that only one R$_1$ may be hydrogen; R$_2$ is lower alkyl; and wherein N, R$_3$ and R$_4$ together with the nitrogen to which they are attached form one of the following: pyrrolyl, imidazolyl, pyrazolyl, dihydropyrazinyl, indolyl, isoindolyl, purinyl, carbazolyl, B-carbolinyl, phenthiazinyl, phenoxozinyl, pyrrolinyl, pyrazolinyl, (o) or (p) isoxazinyl, or imidazolinyl. The total number of carbon atoms in each such hydrocarbyl substituent can range up to about 10. The substituent "Z" contains up to about 5 carbons in the principal chain, e.g. the straight chain of carbons between the terminal valences, but can be branched in that methyl and ethyl substituents can be present on the principal chain. Thus, the alkylene chain Z can contain a total number of carbon atoms greater than 5, preferably no more than about 8.

Heteroaryl as employed herein refers to any heterocyclic structure in which at least one of O, S and N are present as the hetero atoms. These include thiophene, furan, pyridine, thiazole, pyrimidine, pyrrole, benzofuran, quinoline, benzothiophene and substituted heterocycles.

The preferred compounds are those in which the hydrocarbyl radicals contain up to about 7 carbon atoms when aliphatic and up to about 10 carbon atoms when aromatic, e.g., phenyl, tolyl and naphthyl.

The particularly preferred compounds of the invention are those in which Z is —CH₂CH₂— and Ar is a nitrophenyl or trifluoromethylphenyl group, especially 2-trifluoromethylphenyl or 2-nitrophenyl.

The new compounds of the invention can be prepared by art-recognized procedures from known starting compounds as described, for example, in the literature hereinbefore described. The following procedure constitutes a particularly convenient preparative method:

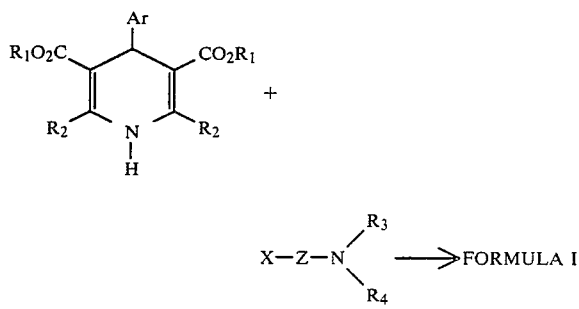

The reaction can be carried out in a solvent in the presence of sodium hydride, or any alkali metal hydride or alkoxide as is commonly employed in condensation reactions. The reaction is effected in two steps, the first, metallation with the alkali metal compound, and the second, condensation with the halide, "X", containing compound, which is usually chloride. The hydrides are convenient since the progress of the metallation reaction can be followed by observing the evolution of hydrogen gas. The metallation step is normally carried out at room temperature. The reaction mixture thereafter is heated at elevated temperature, e.g. at steam bath temperature at or about 100° C., or above up to about 150° C. depending on the boiling point of the selected solvent, and the halide compound is then added, usually in controlled amounts in dropwise fashion and, after addition is completed, the reaction mixture is digested by heating at the elevated temperature.

The product is then obtained in the usual fashion, as by cooling to cause precipitation or evaporation of the solvent to obtain the product as a residue.

The present new compounds can also be prepared by condensation of a compound of the formula:

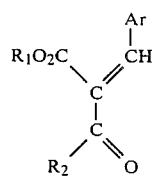

with a compound of the formula:

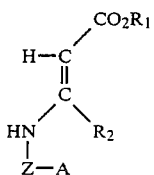

wherein A is the amine moiety described in formula I, and $R_1$, $R_2$, Ar and Z have the same meaning as in formula I.

The condensation reaction between formula V and VI intermediates to form the compounds of formula I is a dehydrating condensation, e.g., it involves splitting out water from the intermediates with the formation of the desired dihydropyridine ring characteristic of the formula I compounds but only when the trans-configuration of structure III compounds is used.

The dehydration can be effected using known dehydrating agents such as silica, preferably in the form of a sieve, e.g., molecular sieve, and is catalyzed by slightly acidic conditions. The slightly acid condition can be effected employing amine hydrohalide salts, e.g., pyridine hydrochloride, diethylaniline hydrochloride, triethylamine hydrochloride, N-methyl piperidine hydrochloride, and corresponding amine sulfonate salts.

Dehydration can also be effected in the presence of reaction solvents which form azeotropes with water, such as toluene, and the water can be removed from the reaction mixture by refluxing and trapping the condensed water using, for example, a Dean Stark apparatus.

The dehydration may also be accomplished by absorption of water as formed by anhydrous salts which form thermally-stable hydrates.

The reaction mixture, including a solvent, is normally heated at elevated temperature for a time sufficient to accomplish significant dehydration. The time of reaction of course is dependent on the selected reaction temperatures. Usually temperatures above about 100° C. are employed, since the use of such temperatures permits reasonable reaction times which can range from 2 hours to 24 hours. It is normally convenient to conduct the reaction at the reflux temperature of the reaction solvent.

Solvents to be employed in the aforesaid reaction include, for example, teriary amines, such as pyridine, N-methylpyrrolidine and N-methylpiperidine, aromatic hydrocarbon solvents such a benzene, toluene and xylene, or tetrahydrofuran, dioxane, dimethylacetamide, acetic acid and lower alkanols such as ethanol and methanol. Of course, mixtures of solvents can be used.

Those compounds in which the respective $R_1$'s differ, e.g., one is methyl and the other ethyl, have a chiral center at the carbon atom to which the Ar group is attached and therefore exist in stereoisomeric forms, i.e., in the "S" and "R" forms.

Such compounds can be prepared by stereospecific synthesis to produce the desired "S" isomer or alternatively as a mixture of the "R" and "S" isomers from which the desired isomer can be separated by known resolution procedures, e.g., by chromatographic techniques. Of course, the mixture of isomers can be used for therapeutic purpose without resolution.

Asymmetric diesters (wherein the respective $R_1$ groups differ) can be prepared by condensation of a compound of the formula:

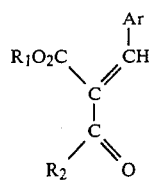

with a compound of the formula:

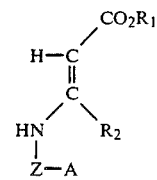

wherein A is the amine moiety described in formula I, and $R_1$, $R_2$, Ar and Z have the same meaning as in formula I, except that the $R_1$ groups must be different.

Employing these procedures, a variety of new unsaturated heterocyclic 1,4-dihydropyridines of the following formula can be prepared:

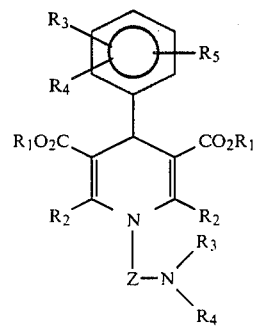

| Z | $R_2$ | $R_1$ | $\underset{R_3 \quad R_4}{N}$ | $R_7$ at 4 position | $R_6$ at 3 position | $R_5$ at 2 position |
|---|---|---|---|---|---|---|
| CHCH$_3$ | CH$_3$ | C$_2$H$_5$ | pyrrolyl | H | H | H |
| CHCH$_3$ | CH$_3$ | C$_2$H$_5$ | imidazolyl | H | CH$_3$ | H |
| CH$_2$CH$_2$ | CH$_3$ | C$_2$H$_5$ | pyrazolyl | H | H | H |
| CH(CH$_3$)CH$_2$ | C$_2$H$_5$ | C$_2$H$_5$ | dihydropyrazinyl | H | H | Cl |
| CH$_2$CH$_2$ | CH$_3$ | i-C$_3$H$_7$ | indolyl | H | CN | H |
| CH$_2$CH$_2$ | CH$_3$ | C$_2$H$_5$ | isoindolyl | H | H | NO$_2$ |
| CH$_2$CH$_2$ | CH$_3$ | C$_2$H$_5$ | purinyl | H | OH | H |
| CH$_2$CH$_2$ | C$_3$H$_7$ | CH$_3$ | carbazolyl | H | H | CF$_3$ |
| CH(CH$_3$) | C$_4$H$_9$ | C$_2$H$_5$ | B—carbolinyl | H | OCH$_3$ | H |
| (CH$_2$)$_3$ | C$_6$H$_{13}$ | C$_2$H$_5$ | phenthiazinyl | H | COOH | H |
| CH$_2$CH$_2$ | i-C$_4$H$_9$ | CH$_3$ | phenoxozinyl | OCH$_3$ | H | H |
| CH$_2$CH$_2$ | CH$_3$ | C$_2$H$_5$ | pyrrolinyl | H | OCH$_3$ | OCH$_3$ |
| (CH$_2$)$_5$ | CH$_3$ | C$_2$H$_5$ | pyrazolinyl | H | CH$_3$ | CH$_3$ |
| CH$_2$CH$_2$ | CH$_3$ | C$_2$H$_5$ | (o) isoxazinyl | H | H | CH$_2$C$_6$H$_5$ |
| CH$_2$CH$_2$ | CH$_3$ | C$_2$H$_5$ | (p) isoxazinyl | H | H | C(CH$_3$)$_3$ |
| CH(CH$_3$)CH$_2$ | CH$_3$ | C$_2$H$_5$ | imidazolinyl | H | H | C$_6$H$_5$ |
| CH$_2$CH$_2$ | CH$_3$ | C$_2$H$_5$ | pyrrolinyl | H | H | H |
| CH$_2$CH$_2$ | CH$_3$ | C$_2$H$_5$ | pyrazolinyl | Cl | Cl | Cl |
| CH$_2$CH$_2$ | CH$_3$ | C$_2$H$_5$ | pyrrolinyl | Cl | H | Cl |
| CH$_2$CH$_2$ | CH$_3$ | C$_2$H$_5$ | phenoxozinyl | Cl | H | Cl |
| CH$_2$CH$_2$ | CH$_3$ | C$_2$H$_5$ | phenthiazinyl | OCH$_3$ | H | CH$_2$=CH—CH$_2$ |
| CH$_2$CH$_2$ | CH$_3$ | C$_2$H$_5$ | B—carbolinyl | H | H | H |
| CH$_2$CH$_2$ | CH$_3$ | C$_2$H$_5$ | carbazolyl | H | CH$_3$ | H |
| CH$_2$CH$_2$ | CH$_3$ | C$_2$H$_5$ | purinyl | H | H | H |
| CH$_2$CH$_2$ | CH$_3$ | C$_2$H$_5$ | isoindolyl | H | H | H |
| CH$_2$CH$_2$ | CH$_3$ | C$_2$H$_5$ | indolyl | H | CH$_3$ | H |
| CH$_2$CH$_2$ | CH$_3$ | C$_2$H$_5$ | pyrazinyl | H | CH$_3$ | CH$_3$ |
| CH$_2$CH$_2$ | CH$_3$ | C$_2$H$_5$ | pyrazolyl | H | H | H |
| CH$_2$CH$_2$ | CH$_3$ | C$_2$H$_5$ | imidazolyl | H | H | H |
| CH$_2$CH$_2$ | CH$_3$ | C$_2$H$_5$ | pyrrolyl | H | CH$_3$ | H |
| CH$_2$CH$_2$ | CH$_3$ | CH$_3$ | pyrrolyl | H | H | OCH$_3$ |
| CH$_2$CH$_2$ | CH$_3$ | CH$_3$ | pyrrolyl | H | H | NO$_2$ |
| CH$_2$CH$_2$ | CH$_3$ | CH$_3$ | pyrazolyl | H | H | OCH$_3$ |
| CH$_2$CH$_2$ | CH$_3$ | CH$_3$ | pyrazolyl | H | H | NO$_2$ |
| CH$_2$CH$_2$ | C$_2$H$_5$ | CH$_3$ | pyrrolyl | H | H | OCH$_3$ |
| CH$_2$CH$_2$ | C$_2$H$_5$ | CH$_3$ | pyrrolyl | H | H | NO$_2$ |
| CH$_2$CH$_2$ | C$_2$H$_5$ | CH$_3$ | pyrazolyl | H | H | NO$_2$ |
| CH$_2$CH$_2$ | C$_2$H$_5$ | CH$_3$ | pyrazolyl | H | H | OCH$_3$ |
| CH$_2$CH$_2$ | CH$_3$ | CH$_3$ | pyrrolyl | H | H | CF$_3$ |
| CH$_2$CH$_2$ | CH$_3$ | CH$_3$ | pyrazolyl | H | H | CF$_3$ |
| CH$_2$CH$_2$ | C$_2$H$_5$ | CH$_3$ | pyrrolyl | H | H | CF$_3$ |
| CH$_2$CH$_2$ | C$_2$H$_5$ | CH$_3$ | pyrazolyl | H | H | CF$_3$ |

-continued

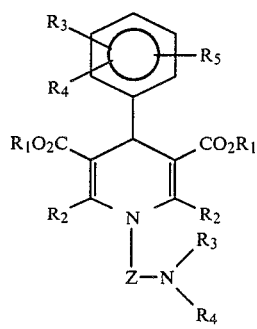

| Z | $R_2$ | $R_1$ | $\underset{R_3\quad R_4}{N}$ | $R_7$ at 4 position | $R_6$ at 3 position | $R_5$ at 2 position |
|---|---|---|---|---|---|---|
| $CH_2CH_2$ | $CH_3$ | $C_2H_5$ | imidazolyl | H | H | Cl |
| $CH_2CH_2$ | $CH_3$ | $C_2H_5$ | dihydropyrazinyl | H | CN | H |
| $CH_2CH_2$ | $CH_3$ | $C_2H_5$ | indolyl | $NO_2$ | H | H |
| $CH_2CH_2$ | $CH_3$ | $C_2H_5$ | isoindolyl | H | OH | H |
| $CH_2CH_2$ | $CH_3$ | $C_2H_5$ | purinyl | H | $CF_3$ | H |
| $CH_2CH_2$ | $CH_3$ | $C_2H_5$ | carbazolyl | H | $OCH_3$ | H |
| $CH_2CH_2$ | $CH_3$ | $C_2H_5$ | phenthiazinyl | H | COOH | H |
| $CH_2CH_2$ | $CH_3$ | $C_2H_5$ | phenoxozinyl | $OCH_3$ | H | H |
| $CH_2CH_2$ | $CH_3$ | $C_2H_5$ | pyrrolinyl | H | $OCH_3$ | $OCH_3$ |
| $CH_2CH_2$ | $CH_3$ | $C_2H_5$ | pyrazolinyl | H | H | $OCH_3$ |
| $CH_2CH_2$ | $CH_3$ | $C_2H_5$ | imidazolinyl | $OCH_3$ | H | $CH_2=CH-CH_2-$ |
| $CH_2CH_2$ | $CH_3$ | $C_2H_5$ | (o) isoxazinyl | H | H | $COOCH_3$ |
| $CH_2CH_2$ | $CH_3$ | $C_2H_5$ | (p) isoxazinyl | $OCH_3$ | H | $COOCH_3$ |
| $CH_2CH_2$ | $CH_3$ | $C_2H_5$ | purinyl | H | H | $-(CH_2)_4-$ |
| $CH_2CH_2$ | $CH_3$ | $C_2H_5$ | isoindolyl | H | H | $NH_2$ |

The present new heterocyclic compounds are therapeutically useful as such or can be employed in the form of salts in view of their basic nature. Thus, these compounds form salts with a wide variety of acids, inorganic and organic, including therapeutically-acceptable acids. The salts with therapeutically-acceptable acids are, of course, useful in the preparation of formulations where water solubility is desired. The salts with therapeutically-unacceptable acids are particularly useful in the isolation and purification of the present new compounds. Therefore, all acid salts of the present new compounds are contemplated by the present invention.

The pharmaceutically-acceptable acid addition salts are of particular value in therapy. These include salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycolic, gluconic, succinic, arylsulfonic, e.g. p-toluenesulfonic acids, and the like. The pharmaceutically-unacceptable acid addition salts, while not useful for therapy, are valuable for isolation and purification of the new substances. Further, they are useful for the preparation of pharmaceutically-acceptable salts. Of this group, the more common salts include those formed with hydrofluoric and perchloric acids. Hydrofluoride salts are particularly useful for the preparation of the pharmaceutically-acceptable salts, e.g., the hydrochlorides, by solution in hydrochloric acid and crystallization of the hydrochloride salt formed. The perchloric acid salts are useful for purification and crystallization of the new products.

As therapeutic agents, the present new heterocyclic compounds are particularly useful as anti-hypertensive agents. The therapeutic agents of this invention may be administered alone or in combination with pharmaceutically-acceptable carriers, the proportion of which is determined by the solubility and chemical nature of the compound, chosen route of administration and standard pharmaceutical practice. For example, they may be administered orally in the form of tablets or capsules containing such excipients as starch, milk sugar, certain types of clay and so forth. They may be administered orally in the form of solutions which may contain coloring and flavoring agents or they may be injected parenterally, that is, intramuscularly, intravenously or subcutaneously. For parenteral administration, they may be used in the form of a sterile solution containing other solutes, for example, enough saline or glucose to make the solution isotonic.

The physician will determine the dosage of the present therapeutic agents which will be most suitable and it will vary with the form of administration and the particular compound chosen, and furthermore, it will vary with the particular patient under treatment. He will generally wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The compounds are useful in the same manner as other anti-hypertensive agents and the dosage level is of the same order of magnitude as is generally employed with these other therapeutic agents. The therapeutic dosage will generally be from 10 to 750 milligrams per day and higher, although it may be administered in several different dosage units. Tablets containing from 10 to 250 mg. of active agent are particularly useful.

The following examples further illustrate the invention.

EXAMPLE I

Diethyl 1,4-dihydro-4-(2-methoxyphenyl)-2,6-dimethyl-1-(2-[1-(3,5-dimethyl)pyrazolyl]ethyl)-3,5-pyridine dicarboxylate To a suspension of sodium hydride (5.2 gms.; 0.11 mole) (50% suspension in mineral oil) in 100 ml of dry distilled DMF is added a solution of diethyl 1,4-dihydro-4-(2-methoxyphenyl)-2,6-dimethyl-3,5-pyridine dicarboxylate (36.1 gms.; 0.1 mole) dissolved in 75 ml of DMF. After the gassing has ceased, the reaction mixture is heated on a water bath for 1½ hours, and then cooled to 50°–60° C. To the warm solution is added a toluene solution of 1-[2-(chloroethyl)]-3,5-dimethylpyrazole (15.8 gms.; 0.1 mole) and the reaction mixture heated at 100° C. for a period of 8 hours. The NaCl and unreacted NaH is filtered off and the solvent removed from the filtrate. The residue is extracted with 2×500 ml portions of hexane. The hexane extracts on cooling yield the crude product. Recrystallization from isopropanol or acetonitrile affords said pyrazoloethyl dihydropyridine.

EXAMPLE II

Diethyl 1,4-dihydro-4-(2-trifluoromethylphenyl)-2,6-dimethyl-1-([2-(3,5-dimethyl)pyrazolyl]ethyl)-3,5-pyridine dicarboxylate By substituting a solution of diethyl 1,4-dihydro-4-(2-trifluoromethylphenyl)-2,6-dimethyl-3,5-pyridine carboxylate for the 2-methoxyphenyl derivative and following the procedure of Example I, said pyrazoloethyl dihydropyridine is obtained.

EXAMPLE III

Diethyl 1,4-dihydro-4-(2-nitrophenyl)-2,6-dimethyl-1-([2-(3,5-dimethyl)pyrazolyl]ethyl)-3,5-pyridine dicarboxylate By substituting a solution of diethyl 1,4-dihydro-4-(2-nitrophenyl)-2,6-dimethyl-3,5-pyridine dicarboxylate for the 2-methoxyphenyl derivative and following the procedure of Example I, said pyrazoloethyl dihydropyridine is obtained.

EXAMPLE IV

Diethyl 1,4-dihydro-4-(2-methoxyphenyl)-2,6-dimethyl-1-(2-[1-pyrrolyl]ethyl)-3,5-pyridine dicarboxylate To a suspension of sodium hydride (5.2 gms.; 0.11 mole) (50% suspension in mineral oil) in 100 ml of dry distilled DMF is added a solution of diethyl 1,4-dihydro-4-(2-methoxyphenyl)-2,6-dimethyl-3,5-pyridine dicarboxylate (36.1 gms.; 0.1 mole) dissolved in 75 ml of DMF. After the gassing has ceased, the reaction mixture is heated on a water bath for 1½ hours, and then cooled to 50°–60° C. To the warm solution is added a toluene solution of 1-[2-(chloroethyl)]pyrrole (12.9 gms.; 0.1 mole) and the reaction mixture heated at 100° C. for a period of 8 hours. The NaCl and unreacted NaH is filtered off and the solvent removed from the filtrate. The residue is extracted with 2×500 ml portions of hexane. The hexane extracts on cooling yield the crude product. Recrystallization from isopropanol or acetonitrile affords the pyrrolyl dihydropyridine.

EXAMPLE V

Diethyl 1,4-dihydro-4-(2-trifluoromethylphenyl)-2,6-dimethyl-1-(2-[pyrrolyl]ethyl)-3,5-pyridine dicarboxylate By substituting a solution of diethyl 1,4-dihydro-4-(2-trifluoromethylphenyl)-2,6-dimethyl-3,5-pyridine dicarboxylate for the 2-methoxyphenyl derivative and following the procedure of Example IV, said pyrrolyl dihydropyridine is obtained.

EXAMPLE VI

Diethyl 1,4-dihydro-4-(2-nitrophenyl)-2,6-dimethyl-1-(2-[pyrrolyl]ethyl)-3,5-pyridine dicarboxylate By substituting a solution of diethyl 1,4-dihydro-4-(2-nitrophenyl)-2,6-dimethyl-3,5-pyridine dicarboxylate for the 2-methoxyphenyl derivative and following the procedure of Example IV, said pyrrolyl dihydropyridine is obtained.

What is claimed is:

1. A compound of the formula

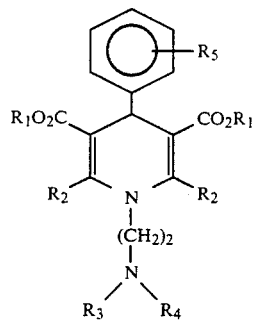

wherein,
$R_1$ is $C_1$–$C_3$ alkyl,
$R_2$ is $C_1$–$C_6$ alkyl,
$R_5$ is H, hydroxy, nitro, cyano, $C_1$–$C_7$ alkoxy, trifluoromethyl, $C_1$–$C_7$ alkyl, halo, or phenyl, and
wherein N, $R_3$ and $R_4$ together form 1-pyrrolyl, 1-(3,5-dimethylpyrazolyl) or 1-pyrazolyl and pharmaceutically acceptable acid addition salts thereof.

2. A compound of claim 1 wherein $R_5$ is at the ortho position.

3. The compound according to claim 1 wherein $R_5$ is a trifluoromethylphenyl.

4. The compound according to claim 1 wherein $R_5$ is nitrophenyl.

5. The compound according to claim 1 wherein $R_5$ is methoxyphenyl.

6. Dimethyl 1,4-dihydro-4-(2-nitrophenyl)-2,6-dimethyl-1-(2[1-(3,5-dimethyl)pyrazolyl]ethyl)-3,5-pyridine dicarboxylate.

7. A pharmaceutically-acceptable acid addition salt of the compound of claim 6.

8. Diethyl 1,4-dihydro-4-(2-trifluoromethylphenyl)-2,6-dimethyl-1-(2[1-pyrrolyl]ethyl)-3,5-pyridine dicarboxylate.

9. A pharmaceutically-acceptable acid addition salt of the compound of claim 8.

10. An anti-hypertensive composition comprising an effective amount of a compound of claim 1 and an inert carrier.

* * * * *